(12) United States Patent
Hyeon et al.

(10) Patent No.: US 9,169,355 B2
(45) Date of Patent: *Oct. 27, 2015

(54) BIOCOMPATIBLE AGENT FOR DISPERSING NANOPARTICLES INTO AN AQUEOUS MEDIUM USING MUSSEL ADHESIVE PROTEIN-MIMETIC POLYMER

(75) Inventors: Taeghwan Hyeon, Seoul (KR); Kun Na, Bucheon-si (KR); Daishun Ling, Seoul (KR); Wooram Park, Gunpo-si (KR)

(73) Assignee: Hanwha Chemical Corporation, Seoul (KR)

( * ) Notice: Subject to any disclaimer, the term of this patent is extended or adjusted under 35 U.S.C. 154(b) by 196 days.

This patent is subject to a terminal disclaimer.

(21) Appl. No.: 13/976,705

(22) PCT Filed: Dec. 28, 2011

(86) PCT No.: PCT/KR2011/010230
§ 371 (c)(1),
(2), (4) Date: Jun. 27, 2013

(87) PCT Pub. No.: WO2012/091452
PCT Pub. Date: Jul. 5, 2012

(65) Prior Publication Data
US 2013/0272965 A1 Oct. 17, 2013

(30) Foreign Application Priority Data
Dec. 29, 2010 (KR) .................. 10-2010-0137829

(51) Int. Cl.
| | | |
|---|---|---|
| A61K 8/00 | (2006.01) | |
| C08G 73/02 | (2006.01) | |
| A61K 49/18 | (2006.01) | |
| C08L 71/02 | (2006.01) | |
| C08G 81/00 | (2006.01) | |
| A61K 8/91 | (2006.01) | |

(52) U.S. Cl.
CPC .......... *C08G 73/024* (2013.01); *A61K 49/1857* (2013.01); *A61K 49/1887* (2013.01); *C08G 73/02* (2013.01); *C08G 81/00* (2013.01); *C08L 71/02* (2013.01); *A61K 8/91* (2013.01); *C08G 2261/128* (2013.01); *C08L 2205/03* (2013.01)

(58) Field of Classification Search
None
See application file for complete search history.

(56) References Cited

U.S. PATENT DOCUMENTS

| | | |
|---|---|---|
| 6,284,267 B1 | 9/2001 | Aneja |
| 2003/0059465 A1 | 3/2003 | Unger et al. |
| 2006/0009550 A1 | 1/2006 | Messersmith et al. |
| 2006/0083781 A1 | 4/2006 | Shastri et al. |
| 2007/0237911 A1 | 10/2007 | Nakano |
| 2009/0280063 A1* | 11/2009 | Kulkarni et al. ............... 424/9.3 |

FOREIGN PATENT DOCUMENTS

| | | |
|---|---|---|
| EP | 2723392 | 4/2014 |
| JP | 2008069092 | 3/2008 |
| WO | 2009135937 A2 | 11/2009 |
| WO | 2012177039 A2 | 12/2012 |

OTHER PUBLICATIONS

Dalsin et al. "Protein Resistance of Titanium Oxide Surfaces Modified by Biologically Inspired mPEG-DOPA", 2005, Langmuir, vol. 21, No. 2, pp. 640-646.*

Ling, D., et al., "Multiple-Interaction Ligands Inspired by Mussel Adhesive Protein: Synthesis of Highly Stable and Biocompatible Nanoparticles," Angewandte Chemie International Edition, vol. 50, No. 48, (2011) pp. 11360-11365.

Kim et al., Phosphine Oxide Polymer for Water-Soluble Nanoparticles, J. Am. Chem. Soc., 2005, pp. 4556-4557, vol. 127.

Yl et al., Silica-Coated Nanocomposites of Magnetic Nanoparticles and Quantum Dots, J. Am. Chem. Soc., 2005, pp. 4990-4991, vol. 127.

* cited by examiner

*Primary Examiner* — James Rogers
(74) *Attorney, Agent, or Firm* — The Webb Law Firm

(57) ABSTRACT

Provided are a mussel adhesive protein-mimetic dispersion stabilizing agent to disperse nanoparticles in an aqueous medium, a colloidal solution including nanoparticles dispersed and stabilized by the dispersion stabilizing agent, and a contrast agent including the colloidal solution. More particularly, the mussel adhesive protein-mimetic dispersion stabilizer is a polyethyleneimine-graft-(poly-ethyleneglycol; polyDOPA) PEI-graft-(PEG;PDOPA). The graft polymer is formed of two parts. One is polyethyleneglycol grafted with a polyethyleneime which has an affinity to an aqueous medium, and the other is polyDOPA which has an affinity to the surface of nanoparticles. Because of those characteristics, the stabilizer shows a stable dispersion of nano particles in the aqueous medium.

19 Claims, 10 Drawing Sheets

BIOCOMPATIBLE AGENT FOR DISPERSING NANOPARTICLES INTO AN AQUEOUS MEDIUM USING MUSSEL ADHESIVE PROTEIN-MIMETIC POLYMER

CROSS-REFERENCE TO RELATED APPLICATIONS

This application is a U.S. national phase under 35 U.S.C. §371 of International Application No. PCT/KR2011/010230 filed Dec. 28, 2011, entitled "Biocompatible Agent for Dispersing Nanoparticles into an Aqueous Medium Using Mussel Adhesive Protein-Mimetic Polymer" and claims priority under 35 U.S.C. §119(a)-(d) to Korean Patent Application No. 10-2010-0137829, filed on Dec. 29, 2010 in the Korean Intellectual Property Office, which are hereby incorporated by reference in their entirety.

TECHNICAL FIELD

The present invention relates to a mussel adhesive protein-mimetic dispersion stabilizing agent ('stabilizer') to disperse nanoparticles in an aqueous medium, a colloidal solution including nanoparticles dispersed and stabilized by the dispersion stabilizing agent, and a contrast agent including the colloidal solution. More particularly, the mussel adhesive protein-mimetic dispersion stabilizer is a polyethyleneimine-graft-(polyethyleneglycol;polyDOPA) (PEI-graft-(PEG; PDOPA)). The graft polymer is composed of two parts, one is including polyethyleneimine grafted with a polyethyleneglycol-based biocompatible polymer, which has an affinity to an aqueous medium (sometimes, abbrev. to 'polyethyleneglycol grafted polyethyleneimine'), and the other is polyDOPA, which has an affinity to the surface of nanoparticles. Because of those characteristics, the stabilizer shows a stable dispersion of nano particles in the aqueous medium.

BACKGROUND ART

Nanoparticles are used in a broad range of applications such as nano-electronic convergence technology, in vivo imaging technology, medical applications, etc. Specifically, super-paramagnetic iron oxide nanoparticles are widely used in a variety of biomedical applications including, for example, a magnetic resonance imaging ('MRI') contrast agent, celltherapy, hyperthermia, drug delivery, cell isolation, nucleic acid preparation, or the like.

The most important requirement for application in biomedical applications is primarily to ensure high quality nanoparticles and, in addition, to allow nanoparticles to have excellent dispersibility and dispersion stability in an aqueous medium. Here, the high quality nanoparticle may mean nanoparticles with features of; (i) uniformity of particle size, (ii) easy control of particle size, (iii) particle crystallinity, (iv) possibility in controlling particle morphology, etc.

However, nanoparticles commercially available in the art are mostly synthesized in an aqueous system or may be obtained by synthesis in a gas phase. Nanoparticles generated by the foregoing processes have difficulty in preparing particles with a uniform shape and generally show deteriorated crystallinity. Further, it is difficult to manufacture nanoparticles having a uniform size and control the size of a particle.

Recently, numerous studies have been executed to develop a novel method for manufacturing metal oxide nanoparticles in an organic system, which have relatively high quality, that is, uniform size and favorable crystallinity, compared to nanoparticles synthesized in an aqueous system according to the related art.

As such, in the case where nanoparticles are synthesized in an organic solvent, uniformity and size control of the nanoparticles may sometimes be achieved by stabilization thereof using an organic additive during a synthesizing process. In this regard, since the surface condition of nanoparticles is influenced by a hydrophobic portion of an organic additive, the metal oxide nanoparticles may be easily dispersed in a hydrophobic organic solvent. However, when they are mixed with water, they do not have sufficient stability.

For such nanoparticles prepared in an organic solvent, hydrophobic properties of the surface of the nanoparticles may obscure stable dispersion of the nanoparticles in water, thus causing a problem for use in biomedical applications. Therefore, in order to use the nanoparticles in the foregoing applications, there is a need to develop a biocompatible dispersion stabilizer that reforms (or modifies) the surface of the nanoparticles in order to have hydrophilic properties and ensures a suitable condition so as to be homogeneously dispersed in an aqueous medium. In addition, development of a nanoparticle dispersion stabilizer that is prepared using the biocompatible dispersion stabilizer described above, wherein the dispersion state is stably maintained in an aqueous system, is also required.

Among methods for dispersing nanoparticles in an aqueous system according to techniques in the related art, use of a thin silica layer has currently been disclosed in the Journal of American Chemical Society, 2005, 127, 4990. According to the foregoing article, polyoxyethylene nonylphenylether is introduced to a cyclohexane solution and mixed with the same to form micro-micelle emulsion drops. Next, a sol-gel reaction of tetraethyl ortho-silicate (TEOS) is induced and nanoparticles are coated with a silica layer and dispersed in water. The above document described a process of coating the outer side of the nanoparticles with a hydrophilic silica layer to disperse the nanoparticles in water, wherein the nanoparticles were prepared in an organic solvent. In this case, the silica coating method using micro-emulsion entails a problem in that, since an amount of nanoparticles to be coated at just one time is very small, an amount of nanoparticle dispersion in an aqueous system manufactured in a single process is also greatly reduced. Moreover, according to the amount of nanoparticle colloids manufactured in the single process or an amount of polyoxyethylene nonylphenylether, conditions of the micro-emulsion are altered. Therefore, there are difficulties in finely regulating a desired thickness of a silica layer, and attaining uniformity of the coated particles since the number of nanoparticles contained in the silica layer is altered. In the case where nanoparticles are stabilized by a silica layer, the foregoing techniques in the related art entail problems in that silane functional groups on the surface of the silica are not sufficiently stable but react to one another, therefore, the nanoparticles coated with the silica and dispersed in water were combined and became agglomerated over time. As a result, it was difficult to ensure storage stability of the dispersion over a long period of time.

In recent years, a method for dispersing nanoparticles in water using a polymer composed of phosphine oxide and polyethyleneglycol has been disclosed in the Journal of America Chemical Society (2005, 127, 4556). More particularly, the foregoing article described a nanoparticle dispersing method wherein, after reacting polyethyleneglycol with 1,2-bis(dichlorophosphino)ethane to synthesize a polymer having polyethyleneglycols bonded together, the polymer is subjected to a ligand exchange reaction with nanoparticles dispersed in a hydrophobic solvent, thereby enabling dispersion stabilization of the nanoparticles and uniformly dispersing the same in water. The disclosed method uses a simple preparation method and utilizes ligand exchange to disperse nanoparticles in water. However, since phosphorus atom (P) is likely to oxidize and become a phosphoryl group, a coating polymer must be synthesized in an inert atmosphere using nitrogen or argon. Further, since the polymer is in a cross-linked state, a problem in introducing a functional group to bond functional ligands in vivo such as DNA, RNA, a monoclonal antibody or other functional proteins, still remains.

Scientists have recently conducted a number of studies upon mussels as a potential origin of bio-adhesives. Mussels generate and secrete a sticky material which is functionally differentiated to allow the mussels to be stationary or anchor in the water, in a marine environment having characteristics of salinity, humidity, tidal flow, turbulent flow, waves, etc. The mussel strongly adheres to the surface of a material in water, using threads composed of a fiber bundle secreted from legs thereof. At the end of each fiber, a plaque comprising a water-proof adhesive is present to allow the mussel to adhere to a wet solid surface. Such thread protein contains a large quantity of 3,4-dihydroxyphynyl-L-alanine (DOPA), which is an amino acid obtained by hydroxylation of tyrosine groups using a polyphenol oxidase. 3,4-dihydroxyphenyl (catechol) on a side branch of DOPA may create a very strong hydrogen bond with the hydrophilic surface and/or be strongly bonded with metal ions, metal oxides ($Fe^{3+}$, $Mn^{3+}$), semi-metal (silicon), or the like.

DISCLOSURE OF INVENTION

Technical Problem

Therefore, as a result of intensive and extensive efforts to overcome the above problems in the related art, the present inventors have completed a biocompatible dispersion stabilizer that can reform the surface of nanoparticles into a hydrophilic state so as to disperse the nanoparticles in an aqueous system and have found that using the same (the stabilizer) may enable the nanoparticles to be dispersed and stabilized ('dispersion stabilization') in the aqueous system, thereby being effectively used for biomedical applications. In addition, it was also found that the nanoparticles dispersed and stabilized by the biocompatible dispersion stabilizer of the present invention may be applicable to a nano-electronic fusion technique field such as a quantum dot (Q-dot) light emitting device, a bio-imaging field such as a MRI contrast agent, a tissue engineering field such as cell therapy, a biomedical field such as hyperthermia, drug delivery, and so forth.

An object of the present invention is to provide a dispersion stabilizer which imitates a mussel protein and reforms the surface of various nanoparticles into a hydrophilic state through a simple process, so as to stabilize dispersion of the nanoparticles in an aqueous medium while enabling application thereof in biomedical fields.

Another object of the present invention is to provide a biocompatible dispersion stabilizer which imitates a mussel protein and includes a branched polymer type polyDOPA, wherein the stabilizer can be stably combined with nanoparticles by a multi-bonding process.

Another object of the present invention is to provide a polyethyleneimine-graft-(polyethyleneglycol;polyDOPA) (PEI-graft-(PEG;PDOPA)), including polyethyleneimine grafted with a polyethyleneglycol-based biocompatible polymer having affinity to an aqueous medium (sometimes, abbrev. to 'polyethyleneglycol grafted polyethyleneimine'), and polyDOPA having affinity to the surface of nanoparticles.

Another object of the present invention is to provide a method for preparing a bio-compatible dispersion stabilizer including a mussel protein-mimetic polymer, that is, a polyethyleneimine-graft-(polyethyleneglycol;polyDOPA).

Another object of the present invention is to provide nanoparticles dispersed in an aqueous medium, using the dispersion stabilizer.

Another object of the present invention is to provide a colloidal solution including nanoparticles dispersed and stabilized in an aqueous medium, by the dispersion stabilizer.

A still further object of the present invention is to provide a contrast agent including the colloidal solution described above.

Solution to Problem

In general aspects, the present invention provides a mussel adhesive protein-mimetic dispersion stabilizer to disperse nanoparticles in an aqueous medium, a colloidal solution including nanoparticles dispersed and stabilized by the above dispersion stabilizer, and a contrast agent including the colloidal solution described above. More particularly, the mussel adhesive protein-mimetic dispersion stabilizer is a polyethyleneimine-graft-(polyethyleneglycol;polyDOPA)(PEI-graft-(PEG;PDOPA)), including polyethyleneimine grafted with a polyethyleneglycol-based biocompatible polymer having affinity to an aqueous medium (sometimes, abbrev. to 'polyethyleneglycol grafted polyethyleneimine'), and polyDOPA having affinity to the surface of nanoparticles.

The present invention also provides a method for preparing a polyethyleneimine-graft-(polyethyleneglycol;polyDOPA), including: (a) combining polyethyleneglycol as a hydrophilic polymer with polyethyleneimine through covalent bonding, to form a polyethyleneimine-graft-polyethyleneglycol; (b) after protecting hydroxyl groups of DOPA, synthesizing DOPA N-carboxyl anhydride (NCA) in the presence of a triphosgene catalyst; and (c) reacting the polyethyleneglycol-polyethyleneimine covalent conjugate prepared in operation (a) and the DOPA N-carboxyl anhydride (NCA) synthesized in operation (b) in an organic solvent, to thus prepare a polyethyleneimine-graft-(polyethyleneglycol;polyDOPA).

In addition, the present invention provides nanoparticles dispersed in an aqueous medium using the polyethyleneimine-graft-(polyethyleneglycol;polyDOPA) as a dispersion stabilizer, and a colloidal solution including the same. Moreover, the present invention provides a contrast agent including the colloidal solution.

Hereinafter, the present invention will be described in more detail.

The mussel adhesive protein-mimetic dispersion stabilizer of the present invention is a polyethyleneimine-graft-(polyethyleneglycol;polyDOPA), including polyethyleneimine grafted with a polyethyleneglycol-based biocompatible polymer having affinity to an aqueous medium (sometimes, abbrev. to 'polyethyleneglycol grafted polyethyleneimine'), and polyDOPA having affinity to the surface of nanoparticles, and contains a mussel adhesive amino acid, that is, DOPA.

In order to prepare the polyethyleneimine-graft-(polyethyleneglycol;polyDOPA) of the present invention, polyethyleneglycol and polyethyleneimine are first combined through covalent bonding to form a polyethyleneimine-graft-polyethyleneglycol. The formed product is used as a biocompatible macro-initiator.

The polyethyleneglycol used in the present invention may be polyethyleneglycol having a number average molecular weight of 300 to 50,000 and a hydroxyl group or carboxyl group at an end thereof. According to one embodiment of the present invention, the polyethyleneglycol is methoxy polyethyleneglycol having a methoxy group at one end and a carboxyl group substituted at the other end.

The polyethyleneimine used in the present invention may be a branched polyethyleneimine without toxicity, which has a number average molecular weight of 100 to 10,100, preferably 100 to 2,000. If the number average molecular weight of the branched polyethyleneimine is less than 100, the produced copolymer of the present invention cannot be suitably combined with a physiologically active material useful therefor. On the other hand, when the number average molecular weight is 10,100 or more, difficulties in excreting the above material out of the body through kidneys may be incurred. Accordingly, the present invention preferably uses polyethyleneimine having a number weight molecular weight present in the foregoing range.

The polyDOPA used in the present invention may be a condensation polymer which has DOPA(3,4-dihydroxyphynylalanine) as a monomer. The repeating units are connected via amide bonds. The number of repeating units ranges from 1 to 100. The polyDOPA may be polymerized by solid phase synthesis and liquid phase synthesis using various coupling methods; carbodiimide-mediated reaction, a symmetrical anhydride method, a mixed anhydride method, an active ester method, an azide method, an acyl-chloride method and an N-carboxy anhydride method. Such example methods which are described hereinbefore are provided to offer a clear understanding of the polyDOPA. However the polyDOPA are not limited to the polymers which are synthesized by the above methods. The polyDOPA used in the present invention may be prepared by the several methods described hereinbefore, preferably by the N-carboxy anhydride method.

The polyethyleneimine-graft-(polyethyleneglycol;polyDOPA) of the present invention may include; a polyethyleneglycol unit represented by the following structure (A), a polyethyleneimine unit represented by the following structure (B), and a polyDOPA unit represented by the following structure (C).

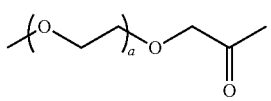

(A)

wherein a ranges from 2 to 1200.

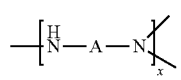

(B)

wherein A is a branched polyethyleneimine and x ranges from 1 to 100.

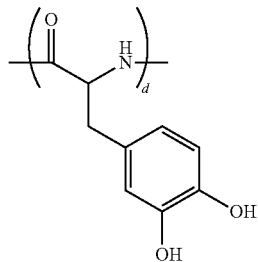

(C)

wherein d ranges from 1 to 100.

The above polyethyleneimine unit (B) may particularly be represented by the following structure.

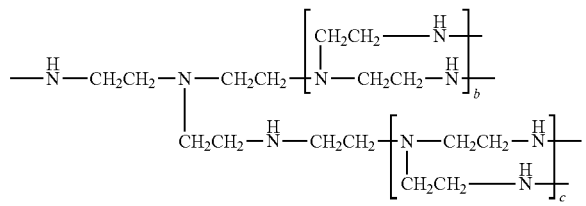

wherein b and c are each independently ranging from 1 to 100, preferably, 1 to 30.

The polyDOPA of the present invention is synthesized from N-carboxyl anhydride of DOPA (NCA) wherein the DOPA is one of the mussel adhesive amino acids and preferably at least one selected from L-DOPA (L-3,4-dihydroxyl phenylalanine) and D-DOPA (D-3,4-dihydroxyl phenylalanine). The polyDOPA may be selected from a group consisting of L-polyDOPA synthesized from N-carboxyl anhydride (NCA) of L-DOPA (L-3,4-dihydroxyl phenylalanine), D-polyDOPA synthesized from N-carboxyl anhydride (NCA) of D-DOPA (D-3,4-dihydroxyl phenylalanine and L,D-polyDOPA synthesiszed from N-carboxyl anhydride (NCA) of L,D-DOPA(L,D-3,4-dihydroxyl phenylalanine, mixture of L-DOPA and D-DOPA).

Operation (a) is a process of preparing a biocompatible macro-initiator used for manufacturing a mussel protein-mimetic polymer for stabilizing nanoparticles. In operation (a), covalent bonding of polyethyleneglycol and polyethyleneimine may be implemented using dicyclohexylcarbodiimide (DCC)/N-hydroxysuccinimide (NHS) or, otherwise, hexamethylene diisocyanate (HMDI). Here, DCC and NHS activate a carboxyl group in polyethyleneglycol having both methoxy and carboxyl group ends, in order to react with a primary amine of polyethyleneimine, thus forming a peptide covalent bond. Alternatively, HMDI activates a hydroxyl group of polyethyleneglycol having a methoxy end and serves to bond it to a primary amine of polyethyleneimine. Covalent bonding between polyethyleneglycol and polyethyleneimine activated by HMDI may include any reaction to form a covalent bond between the foregoing two polymers. In one embodiment of the present invention, after dissolving polyethyleneglycol and polyethyleneimine activated by DCC/NHS in chloroform, respectively, the polyethyleneglycol solution is added drop by drop to the polyethyleneimine solution, thus enabling these two polymers to be covalently bonded. After completing a reaction, the reacted solution is concentrated and precipitated in di-ethylether to produce a covalent conjugate of polyethyleneglycol and polyethyleneimine. A structure of polyethyleneglycol activated by DCC/NHS and a covalent bond structure of the activated polyethyleneglycol and a branch type polyethyleneimine (PEI) are illustrated as follows:

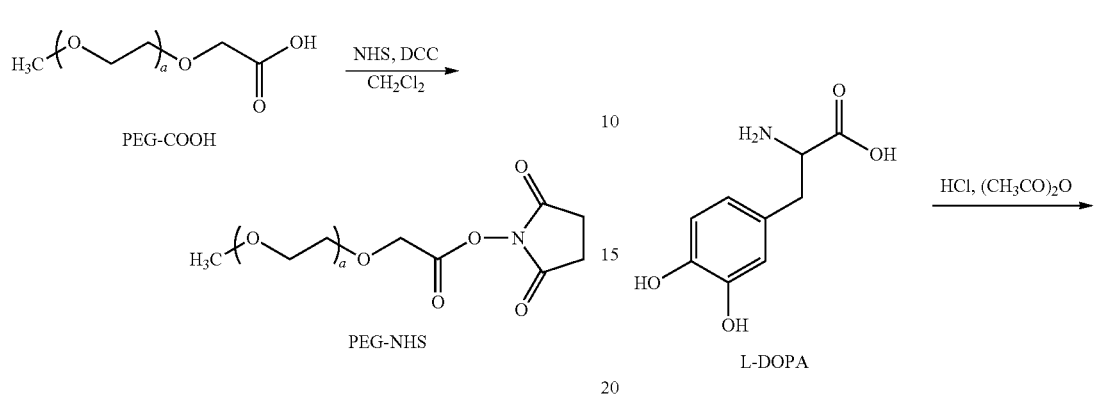

PEG-COOH

PEG-NHS

[wherein, a ranges from 2 to 1200.]
<Activation of polyethyleneglycol (PEG-NHS)>

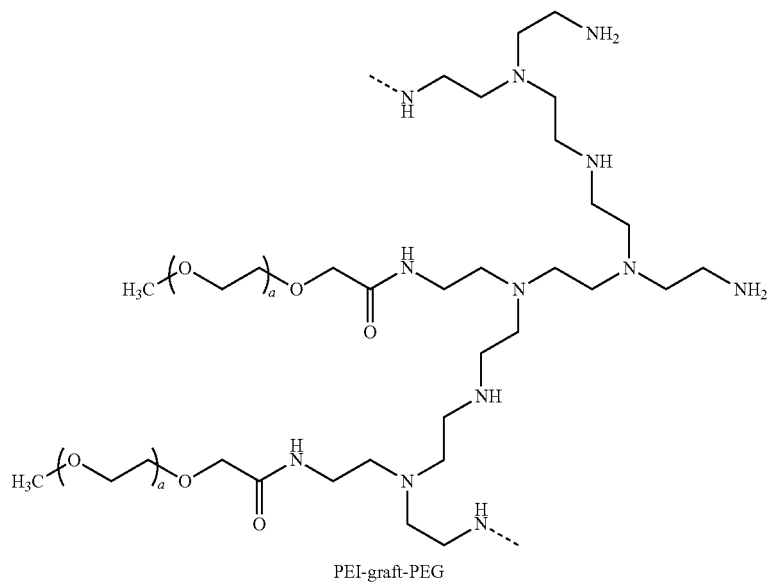

PEI-graft-PEG

[wherein, a ranges from 2 to 1200.]
<polyethyleneimine-graft-polyethyleneglycol (PEI-graft-PEI)>

Synthesis of DOPA N-carboxyl anhydride (NCA) in operation (b) may be executed using at least one selected from the mussel adhesive amino acids, that is, L-DOPA (L-3,4-dihydroxyl phenylalanine) and D-DOPA (D-3,4-dihydroxyl phenylalanine) as a starting material and by any method for preparation of amino acid N-carboxyl anhydride (NCA) known in the related art. Preferably, the foregoing substance (NCA) is prepared by reacting the mussel adhesive amino acid (D-DOPA or L-DOPA or L,D-DOPA) in a proper solvent in the presence of a triphosgene catalyst.

According to one embodiment of the present invention, as illustrated below, L-DOPA is dissolved in acetic acid, using acetic acid anhydride as well as hydrochloric acid, followed by acetylation of a hydroxyl group of L-DOPA to synthesize (AC)$_2$-DOPA while protecting the hydroxyl group. Thereafter, using triphosgene in an organic solvent composed of tetrahydrofurane (THF), N-carboxyl anhydride of L-DOPA (NCA) is synthesized [see below].

L-DOPA

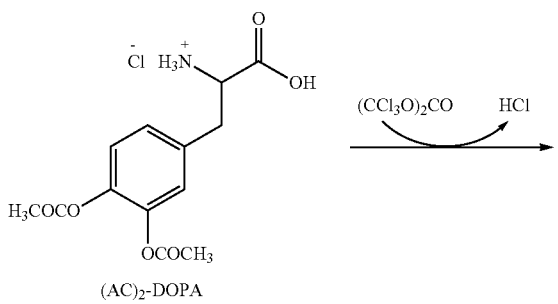

(AC)$_2$-DOPA

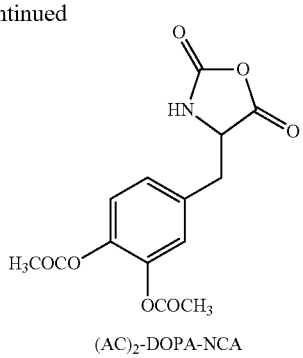

(AC)₂-DOPA-NCA

<Reaction Scheme of DOPA N-carboxyl Anhydride (NCA)>

Preparation of a polyethyleneimine-graft-(polyethyleneglycol;polyDOPA) in operation (c) may be executed by multi-initiation of the polyethyleneimine-graft-polyethyleneglycol formed in operation (a) and the DOPA N-carboxyl anhydride (NCA) synthesized in operation (b) in an organic solvent, enabling polymerization thereof. The poly DOPA in the copolymer is synthesized by inducing polymerization of DOPA N-carboxyl anhydride using the primary amine present in the polyethyleneimine-graft-polyethyleneglycol as a multi-initiator. According to the foregoing processes, the synthesized polyDOPA is combined with the polyethyleneimine-graft-polyethyleneglycol resulting in a final product, that is, the polyethyleneimine-graft-(polyethyleneglycol; polyDOPA).

In operation (c), by regulating an added amount of DOPA N-carboxyl anhydride (NCA) used as a bio-mimetic conjugate site, the copolymer of the present invention may have controlled bonding ability and hydrophobic property ('hydrophobicity'). Preferably, a relative molar ratio of the polyethyleneimine-graft-polyethyleneglycol to DOPA N-carboxyl anhydride (NCA) ranges from 1:1 to 1:50. If the molar ratio is out of the above range, problems of increasing hydrophobicity or decreasing the bonding ability of the bio-mimetic dispersion stabilizer may arise.

The organic solvent used in operation (c) may include at least one selected from dimethyl sulfoxide (DMSO), tetrahydrofuran (THF), and chloroform (ClCH₃).

After completing polymerization in operation (c), operation (d) which is a process for de-protection of a protective hydroxyl group of the polyDOPA may be further included. According to one embodiment of the present invention, after completing polymerization of the polyethyleneimine-graft-(polyethyleneglycol;polyDOPA), the product is dispersed in dimethyl formamide (DMF). Thereafter, by adding a proper amount of piperidine thereto, a hydroxyl group of the DOPA protected with an acetyl group may be de-acetylated, in turn resulting in a polyethyleneimine-graft-(polyethyleneglycol; polyDOPA) represented by the following structure:

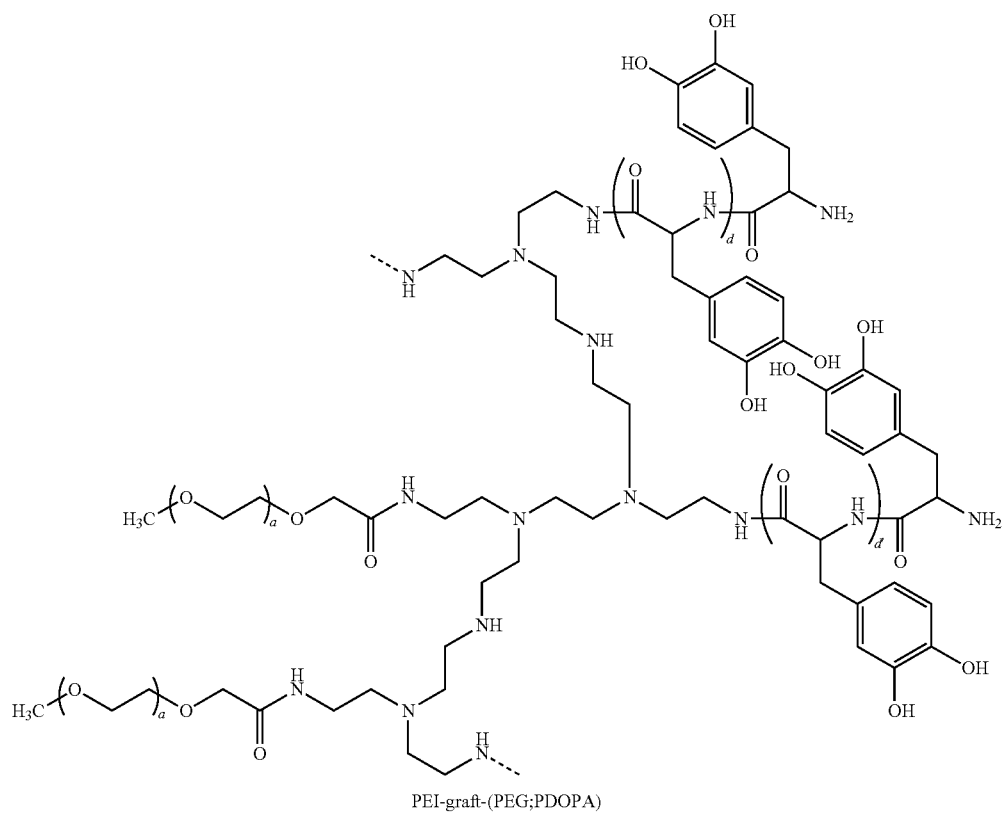

PEI-graft-(PEG;PDOPA)

[wherein a ranges from 2 to 1200, and d and d each independently ranges from 1 to 100.]

<polyethyleneimine-graft-(polyethyleneglycol;poly-DOPA) (PEI-graft-(PEG;PDOPA))>

In addition, provided are nanoparticles dispersed in an aqueous medium using the dispersion stabilizing agent, and a colloidal solution including the nanoparticles.

The polyethyleneimine-graft-(polyethyleneglycol;poly-DOPA) used in the present invention may be a biocompatible branch type dispersion stabilizer comprising a mussel adhesive protein-mimetic biocompatible polymer and containing polyDOPA, and useful in dispersing and stabilizing nanoparticles in an aqueous medium.

Such nanoparticles may include one or more inorganic nanoparticles selected from a group consisting of metal, metal calcogenide, metal oxide, magnetic substances, magnetic alloys, semiconductor materials or multi-component composite structures.

More particularly, the metal may be selected from a group consisting of Pd, Pt, Au, Cu and Ag; the metal calcogenide may be $M_xE_y$ (M=Ti, V, Cr, Mn, Fe, Co, Ni, Cu, Zr, Mo, Ru, Rh, Ag, W, Re, Ta, Hf, Zn or Cd; E=O, S or Se; $0<x\leq 3$; $0<y\leq 5$); and the metal oxide may be selected from a group consisting of titanium oxide, vanadium oxide, chromium oxide, manganese oxide, iron oxide, cobalt oxide, nickel oxide, copper oxide, zirconium oxide, molybdenum oxide, ruthenium oxide, rhodium oxide, silver oxide, tungsten oxide, rhenium oxide, tantalum oxide, hafnium oxide and zinc oxide. More preferably, the iron oxide may be selected from FeO, $Fe_3O_4$(magnetite), $\alpha$-$Fe_2O_3$, $\beta$-$Fe_2O_3$, $\gamma$-$Fe_2O_3$ (maghemite), $\epsilon$-$Fe_2O_3$, $Fe(OH)_2$, $Fe(OH)_3$, $\alpha$-FeOOH, $\beta$-FeOOH, $\gamma$-FeOOH, $\delta$-FeOOH, $Fe_5HO_8 \cdot 4H_2O$, $5Fe_2O_3 \cdot 9H_2O$, $FeOOH \cdot 4H_2O$, $Fe_8O_8(OH)_6(SO) \cdot nH_2O$, $Fe_{16}O_{16}(OH.SO_4)_{12-13} \cdot 10-12H_2O$, and a mixture of $Fe_3O_4$ (magnetite) and $\gamma$-$Fe_2O_3$(maghemite). Alternatively, the magnetic substance is preferably selected from a group consisting of Co, Mn, Fe, Ni, Gd, $MM'_2O_4$ and $M_xO_y$ (M or M'=Co, Fe, Ni, Mn, Zn, Gd, Cr; $0<x\leq 3$; $0<y\leq 5$, respectively); the magnetic alloys are preferably selected from a group consisting of CoCu, CoPt, FePt, CoSm, NiFe and NiFeCo. Meanwhile, the semiconductor material may be selected from a group consisting of: semiconductors comprising elements selected from Group 2 and Group 6, respectively; semiconductors comprising elements selected from Group 3 and Group 5, respectively; semiconductors comprising Group 4 elements; semiconductors comprising elements selected from Group 4 and Group 6, respectively; semiconductors comprising elements selected from Group 5 and Group 6, respectively. The multi-component composite structure may include at least two selected from a group consisting of metal, metal calcogenide, magnetic substances, magnetic alloys and semiconductor materials, in addition, include core-shell or hetero-junction structural materials. More preferably, at least one selected from a group consisting of: cadmium selenide/zinc sulfide core/shell (CdSe/ZnS core/shell), cadmium selenide/zinc selenide core/shell (CdSe/ZnSe core/shell), cadmium selenide/cadmium sulfide core/shell (CdSe/CdS core/shell), cadmium telluride/zinc sulfide core/shell (CdTe/ZnS core/shell), cadmium telluride/zinc selenide core/shell (CdTe/ZnSe core/shell), cadmium telluride/cadmium sulfide core/shell (CdTe/CdS core/shell), cadmium telluride/cadmium selenide core/shell (CdTe/CdSe core/shell), zinc sulfide (ZnS), cadmium sulfide (CdS), indium arsenide (InAs), indium phosphide (InP), indium arsenide/indium phosphide core/shell (InAs/InP core/shell), indium arsenide/cadmium selenide core/shell (InAs/CdSe core/shell), indium arsenide/zinc sulfide core/shell (InAs/ZnS core/shell), indium arsenide/zinc selenide core/shell (InAs/ZnSe core/shell), indium phosphide/cadmium selenide core/shell (InP/CdSe core/shell), indium phosphide/zinc sulfide core/shell (InP/ZnS core/shell), indium phosphide/zinc selenide core/shell (InP/ZnSe core/shell), or the like, may be used.

Also, provided as a contrast agent including the colloidal solution.

Advantageous Effects of Invention

According to the present invention, a mussel adhesive protein-mimetic biocompatible dispersion stabilizer capable of modifying the surface of nanoparticles and stably dispersing the same in an aqueous medium may be synthesized. The dispersion stabilizer prepared according to the present invention has polyDOPA formed through multi-initiative polymerization, in turn having at least one unit of DOPA per molecule, that is multiple interaction ligands (MIL) and exhibiting a high bonding strength to a hydrophilic surface. Since the prepared dispersion stabilizer according to the present invention has a positive charge, it may impart additional electrostatic bonding force to the surface of nanoparticles having a negative charge. Moreover, since numerous polyethyleneglycol molecules having hydrophilic property are bonded to branches of a branch type polyethyleneimine, high aqueous dispersion stabilization may be achieved through hydrophilic property and stereoscopic effects. Accordingly, the biocompatible dispersion stabilizer prepared as described above may enable stable dispersion of nanoparticles in an aqueous medium, thereby being applicable in various fields including, for example: nano-electronic convergence technologies such as Q-Dot light-emitting devices; bio-imaging applications such as a magnetic resonance imaging (MRI) contrast agent; tissue engineering applications such as cell treatment; biomedical applications such as hyperthermia, drug delivery, etc. Further, compared to nanoparticles dispersed by a dispersion stabilizers produced according to conventional techniques, superior dispersion stability may be achieved.

BRIEF DESCRIPTION OF DRAWINGS

The above and other objects, features and advantages of the present invention will become apparent from the following description of preferred embodiments given in conjunction with the accompanying drawings, in which.

MODE FOR THE INVENTION

Figure 1:
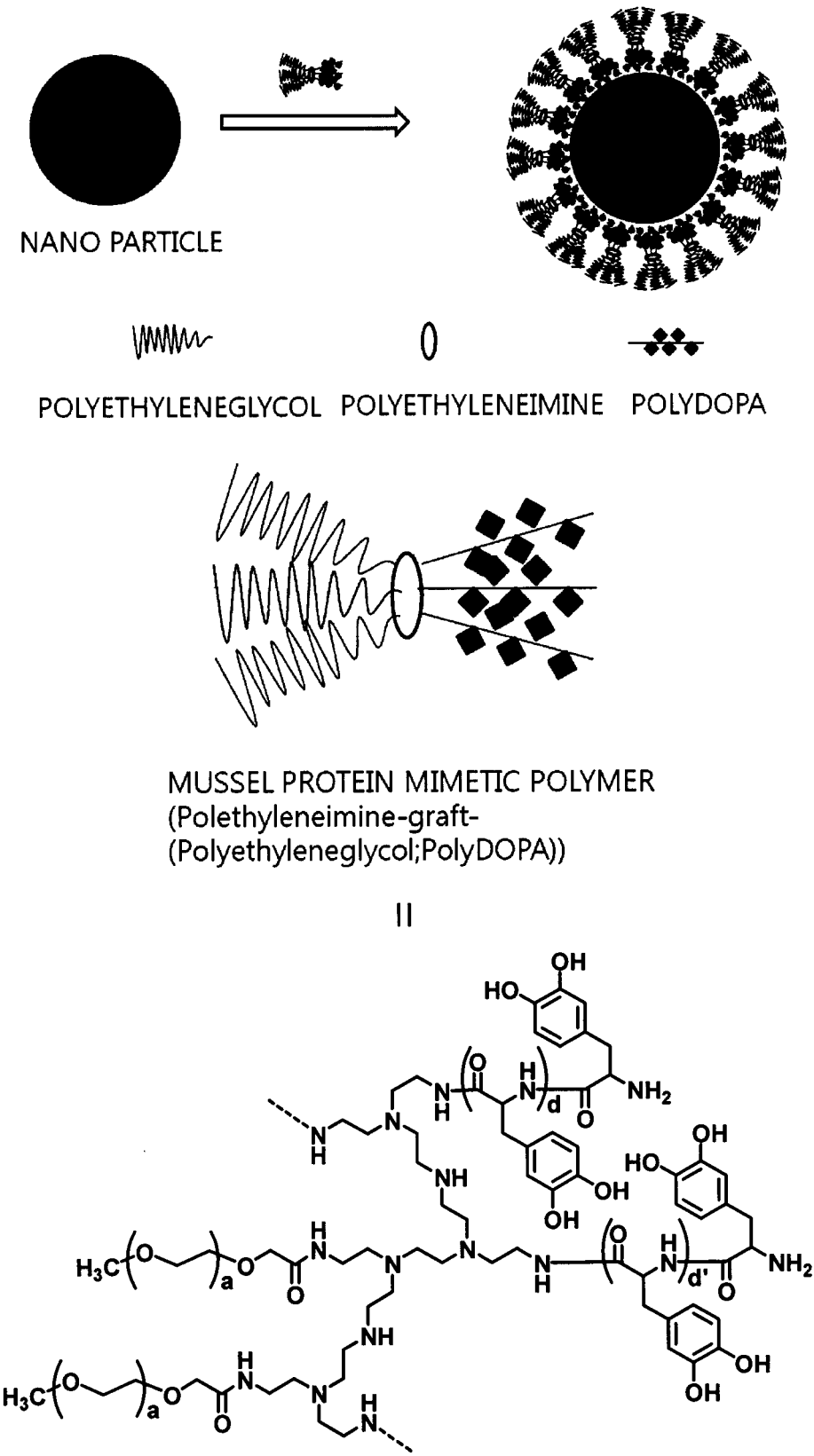
FIG. 1 illustrates a chemical structure of a mussel adhesive protein-mimetic bio-compatible dispersion stabilizer and stabilization of nanoparticles used in the present invention.

The advantages, features and aspects of the present invention will become apparent from the following description of the embodiments with reference to the accompanying drawings, which is set forth hereinafter. However, such embodiments are provided to offer a clearer understanding of the present invention and the scope of technical configurations of the present invention should not be construed as limited to the embodiments set forth herein. Rather, various modifications and/or alterations of principal concepts of the present invention and performance thereof may be easily made by those having ordinary knowledge in the related art.

L-3,4-dihydroxy phenylalanine ('DOPA'), PEG-OH (5,000 Da), dimethyl formamide (DMF) N-hydroxy succinimide (NHS), N,N'-dicyclohexyl carbodiimide (DCC), acetic acid anhydride, glacial acetic acid, methylene chloride (MC) and chloroform were purchased from Sigma Chemical Company (St. Louis, Mo.), and PEI (1,800 Da (PEI 1,800)) was purchased from Alfa Aesar. For 48 hours before use, these materials were dried at 40° C. under vacuum.

Example 1

Synthesis of Mussel Adhesive Protein-Mimetic Biocompatible Dispersion Stabilizer

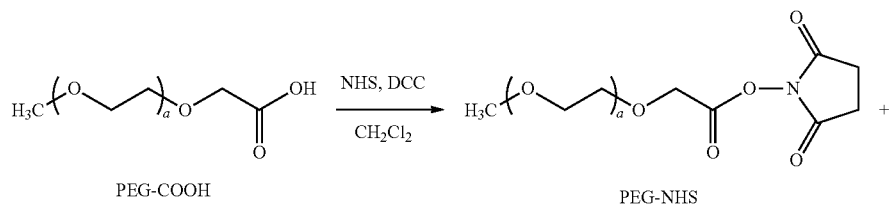

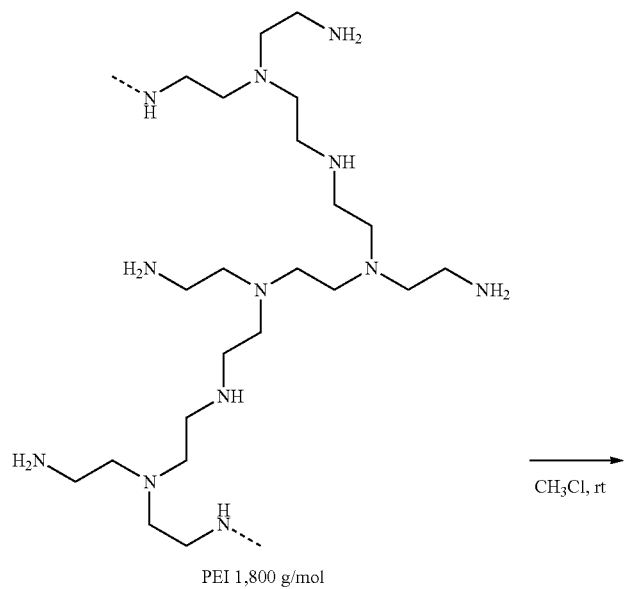

-continued
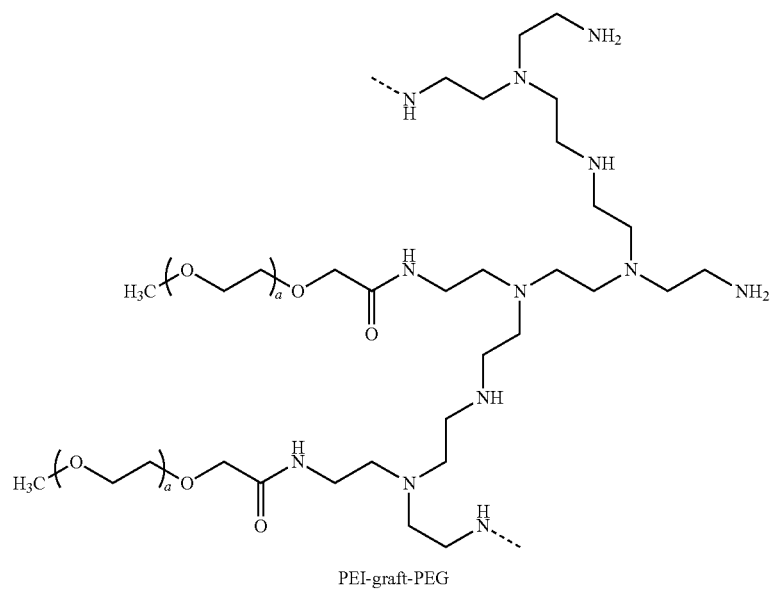
PEI-graft-PEG
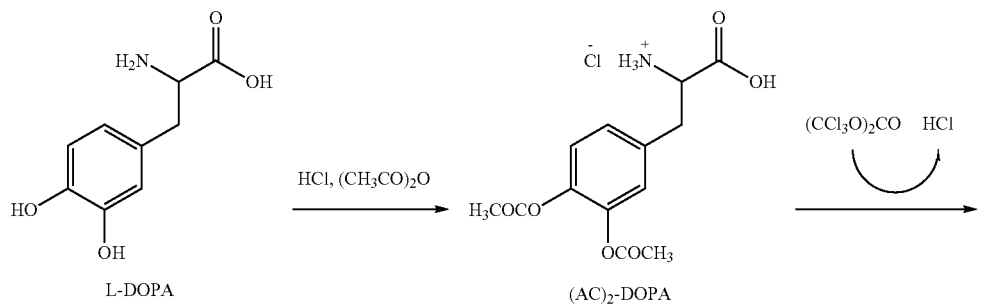
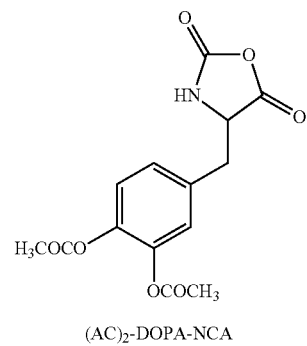
(AC)₂-DOPA-NCA

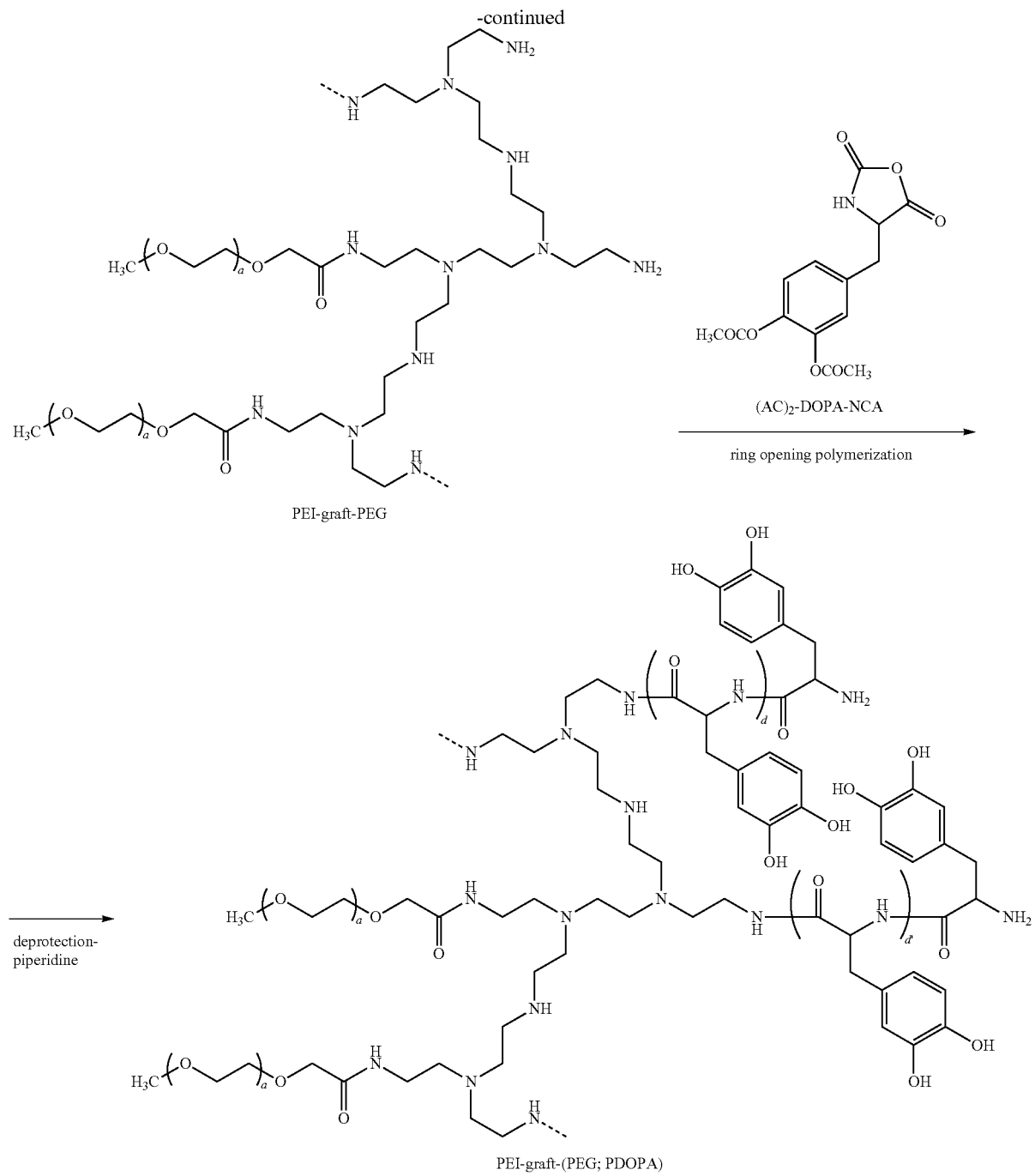

PEI-graft-PEG (AC)₂-DOPA-NCA ring opening polymerization deprotection-piperidine PEI-graft-(PEG; PDOPA)

<1-1> Activation of Polyethyleneglycol
<1-1-1> Use of Dicyclohexylcarbodiimide/N-Hydroxy Succinylimide (DCC/NHS)

After mounting a reflux condenser, methoxy polyethyleneglycol carboxyl (PEG-COOH, 5000) (10 g) was dissolved in methylene chloride (CHCl₂) (50 ml) in a 250 ml flask. Then, N-hydroxysuccinimide (NHS) (0.52 g) and dicyclohexylcarbodiimide (DCC) (0.74 g) were added thereto, followed by a reaction at room temperature for 20 hours. After removing dicyclohexylurea through filtration, this material was precipitated in diethylether, resulting in polyethyleneglycol in an activated state (PEG-NHS). (Yield=87%) ¹H NMR (300 MHz, CDCl₃): δ 4.1 (b, —CO—CH₂—CH₂— CH₂—O—), 3.5-3.8 (m, —CH₂CH₂CO—), 2.8 (b, —CO— CH₂—CH₂—CO—), 1.8 (b, —CO—CH₂—CH₂—CH₂— CH₂—CH₂—O—), 1.2 (b, —CO—CH₂—CH₂—CH₂— CH₂—CH₂—O—).

<1-1-2> Use of Hexamethylene Diisocyanate (HDMI)

After mounting a reflux condenser, methoxy polyethyleneglycol (PEG-OH) (15.23 g) was dissolved in chloroform (CHCl₃) (15 ml) in a 100 ml flask. Then, the solution was treated using hexamethylene diisocyanate (HMDI) (60 ml), followed by a reaction for 24 hours to prepare a polymer. After completing the reaction, the polymer was precipitated in petroleum ether to purify the same and, after washing with petroleum ether (400 ml) three times, the washed material was dissolved again in chloroform ($CHCl_3$) (20 ml). After then, the solution was precipitated again in petroleum ether (500 ml) to purify the same. The foregoing procedure was repeated 10 times, followed by drying under vacuum, resulting in polyethyleneglycol in an activated state (Yield=80%).

<1-2> Formation of a Polyethyleneimine-Graft-Polyethyleneglycol (PEI-Graft-PEG)

The activated polyethyleneglycol (PEG-NHS) (2 g) obtained in Example <1-1> was dissolved in chloroform (200 ml). Then, after dissolving polyethyleneimine (Alfa Aesar, 1800 da, 0.5 g) in chloroform (50 ml), the polyethyleneglycol solution was added drop by drop thereto to conduct a covalent bonding reaction between polyethyleneglycol and polyethyleneimine. Here, the reaction was executed for 24 hours and, after completing the reaction, the resultant product was concentrated to reach a total volume of 30 ml by a vacuum concentrator. Following this, the concentrated material was precipitated in diethylether to obtain a polyethyleneimine-graft-polyethyleneglycol (PEI-graft-PEI). (Yield=85%) $^1$H NMR (300 MHz, $D_2O$). As a result of measurement (—$CH_2CH_2O$— of PEG at 3.5-3.8 ppm and —$CH_2CH_2NH$— of PEI at 2.5-3.2 ppm), M, of PEI-graft-PEG was found to be about 41,800 Da. It was presumed that each PEI-graft-PEG has almost 8 (hereinafter, referred to as $PEI_1$-graft-$PEG_8$). $^1$H NMR (300 MHz, $D_2O$): δ 3.5-3.8 (m, —$CH_2CH_2O$—), 3.5-3.8 (m, —$CH_2CH_2O$—), 3.3 (s, $CH_3O$—), 2.5-3.2 (m, —$CH_2CH_2NH$—).

<1-3> Protection of Hydroxyl Group of DOPA Amino Acid

L-DOPA (3 g) was suspended in glacial acetic acid (100 ml), followed by purging dried gas of hydrochloric acid at room temperature for 5 hours. After adding acetic acid anhydride (3 ml) and reacting at room temperature for 1 hour 30 minutes, 3 ml of acetic acid anhydride was further added and a reaction was conducted in an oil bath at 60° C. for 30 minutes. The reaction product was concentrated in a vacuum concentrator and unreacted acetic acid anhydride was removed by adding ethanol. Thereafter, the remaining product was precipitated in diethylether to obtain DOPA amino acid having a protected hydroxyl group ($DOPA(Ac)_2$). (Yield=80%) $^1$H NMR (300 MHz, $D_2O$): δ 6.7-6.9 (m, —$C_6H_3(OH)_2$), 4.0 (m, $C_6H_3(OH)_2$—$CH_2$—CH(N—)—C(O)N—), 3.2 (m, $C_6H_3(OH)_2$—$CH_2$—CH—), 2.4 (s, $CH_3(CO)$—).

<1-4> Synthesis of DOPA Amino Acid N-Carboxyl Anhydride (NCA)

0.5 g of the DOPA amino acid having a protected hydroxyl group synthesized in Example <1-3> as well as 0.5 g of triphosgene were dispersed in THF (50 ml) and reacted in an oil bath at 60° C. Next, the reaction product was precipitated in hexane (800 ml), dissolved in THF (50 ml) and precipitated again in hexane. The foregoing procedure was repeated three times. After purifying, the product was dried using a vacuum dryer, resulting in DOPA N-carboxyl anhydride (DOPA ($AC_2$)—NCA). (Yield=65%) $^1$H NMR (300 MHz, DMSO): δ 6.2-6.9 (m, —$C_6H_3(OH)_2$), 4.3 (t, —NHCH CO—), 3.7 (m, $C_6H_3(OH)_2$—$CH_2$—CH(N—)—C(O)N—), 3.3 (m, $C_6H_3(OH)_2$—$CH_2$—CH—), 2.4 (s, $CH_3(CO)$—).

<1-5> Synthesis of Polyethyleneimine-Graft-(Polyethyleneglycol;polyDOPA) (PEI-Graft-(PEG;PDOPA))

0.5 g of the polyethyleneimine-graft-polyethyleneglycol (PEI-graft-PEG) prepared in Example <1-2> and the DOPA N-carboxyl anhydride ($DOPA(AC_2)$—NCA) prepared in Example <1-4> were used in different molar ratios (1:5 and 1:15, respectively) and reacted in THF solvent, thus synthesizing a polyethyleneimine-graft-(polyethyleneglycol;polyDOPA) (Yield, molar ratio 1:5=85%, molar ratio 1:15=87%).

<1-6> De-Protection of Polyethyleneimine-Graft-(Polyethyleneglycol;polyDOPA)

Figure 2:
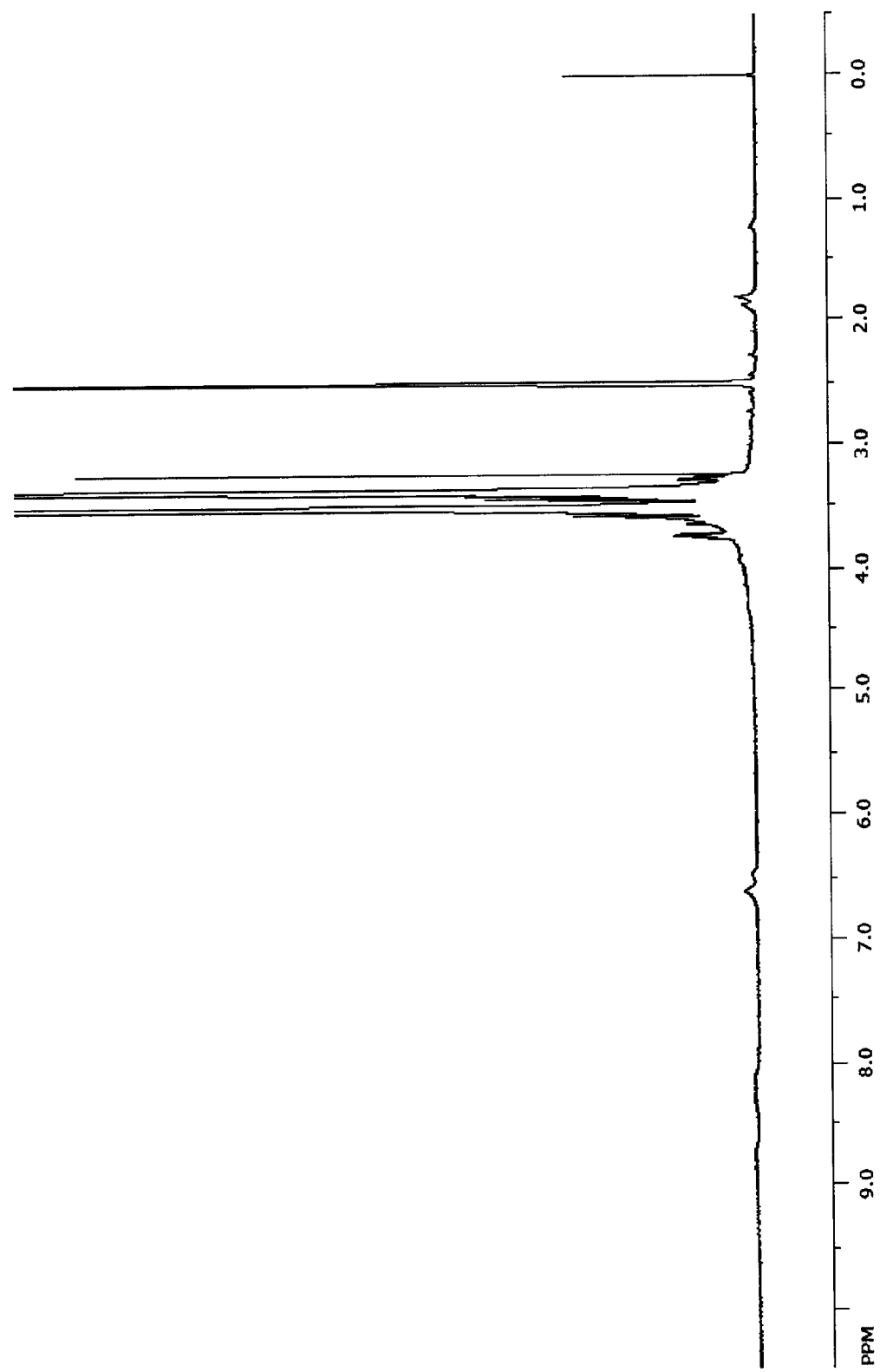
FIG. 2 illustrates analyzed results of $^1$H-NMR (in DMSO) of PEI-graft-(PEG;PDOPAs) prepared in Example <1-6>.
Figure 3:
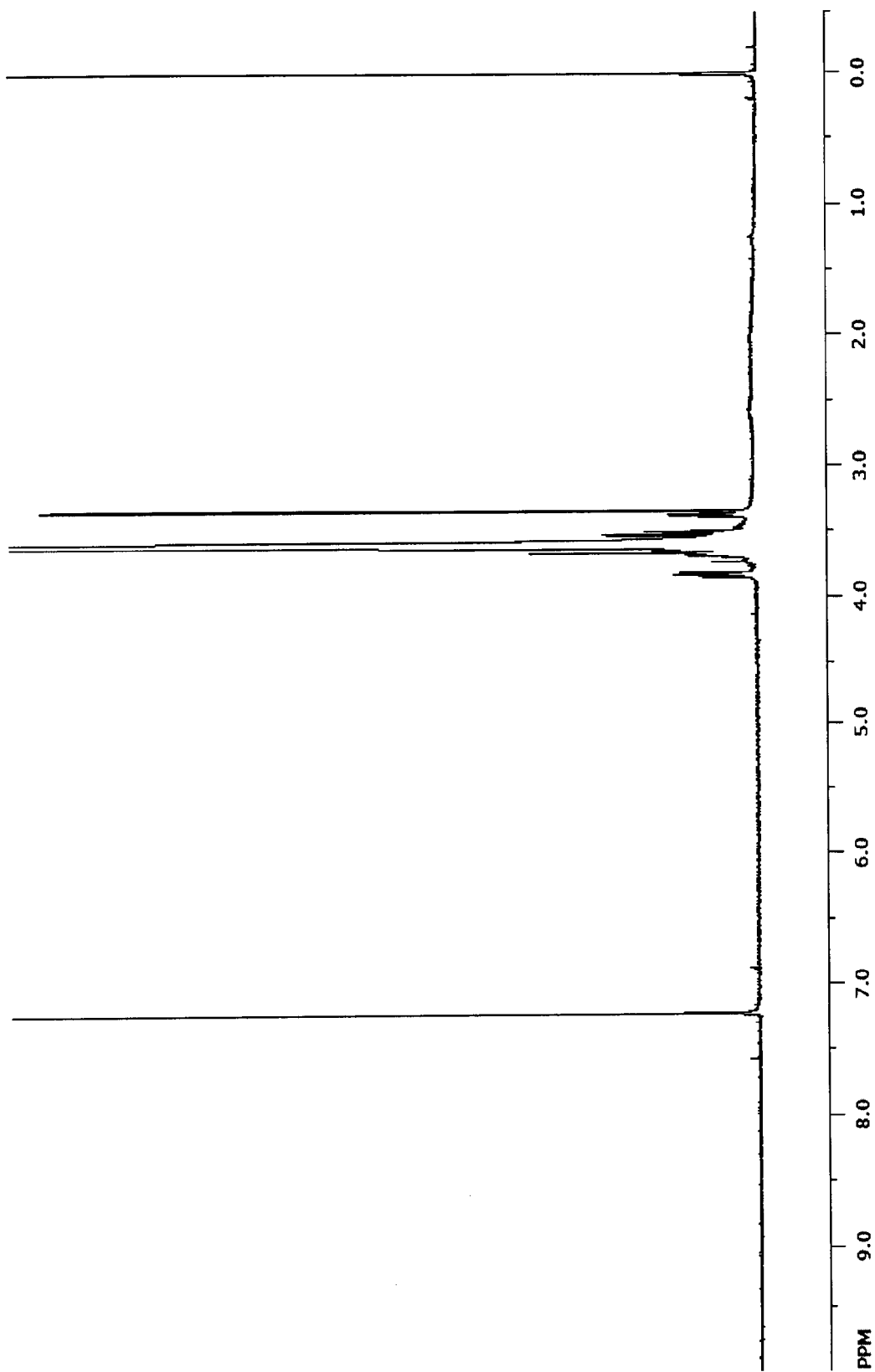
FIG. 3 illustrates analyzed results of $^1$H-NMR (in $CDCl_3$) of PEI-graft-(PEG;$PDOPA_5$) prepared in Example <1-6>.
Figure 4:
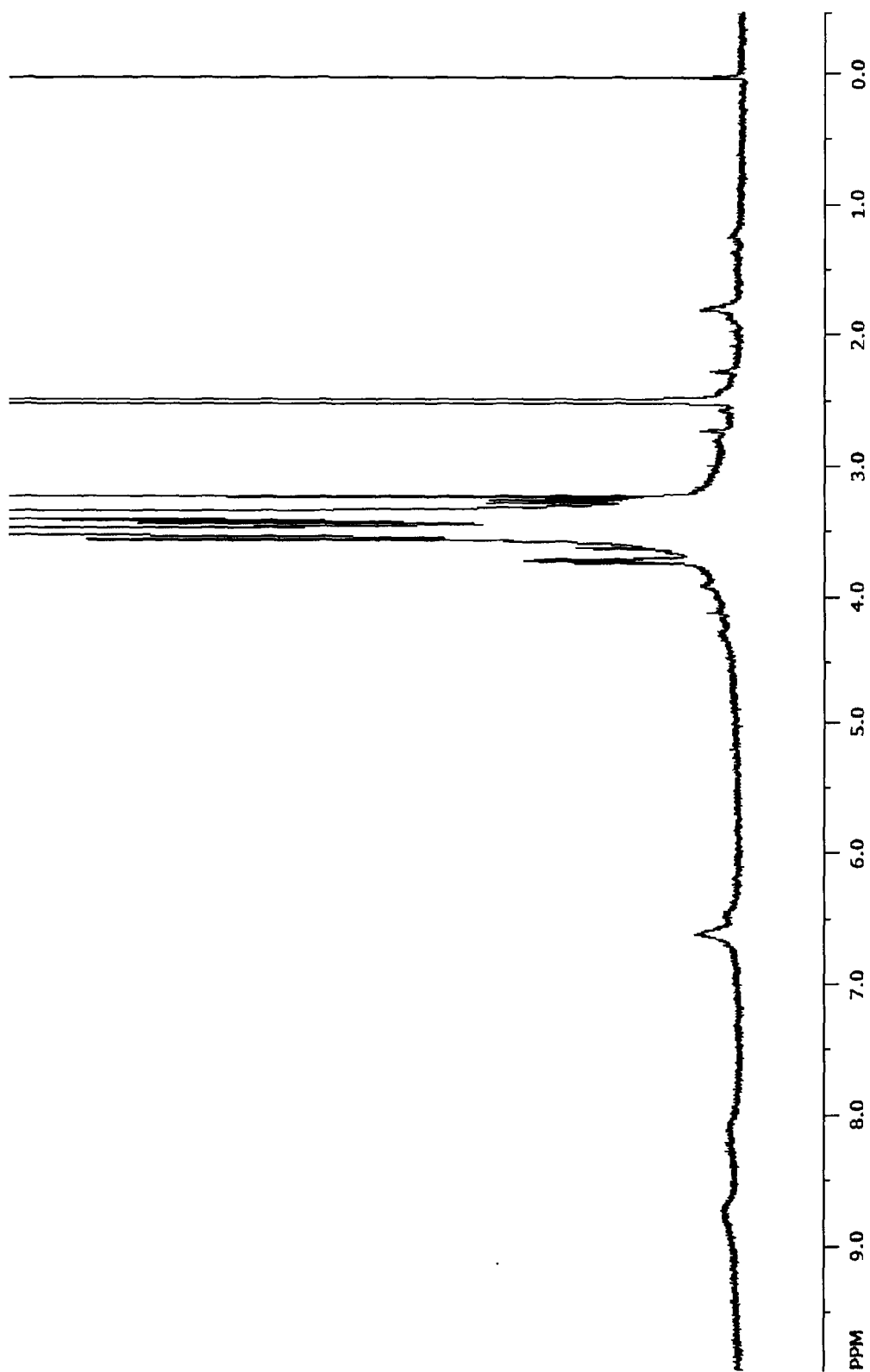
FIG. 4 illustrates analyzed results of $^1$H-NMR (in DMSO) of PEI-graft-(PEG;$PDOPA_{15}$) prepared in Example <1-6>.
Figure 5:
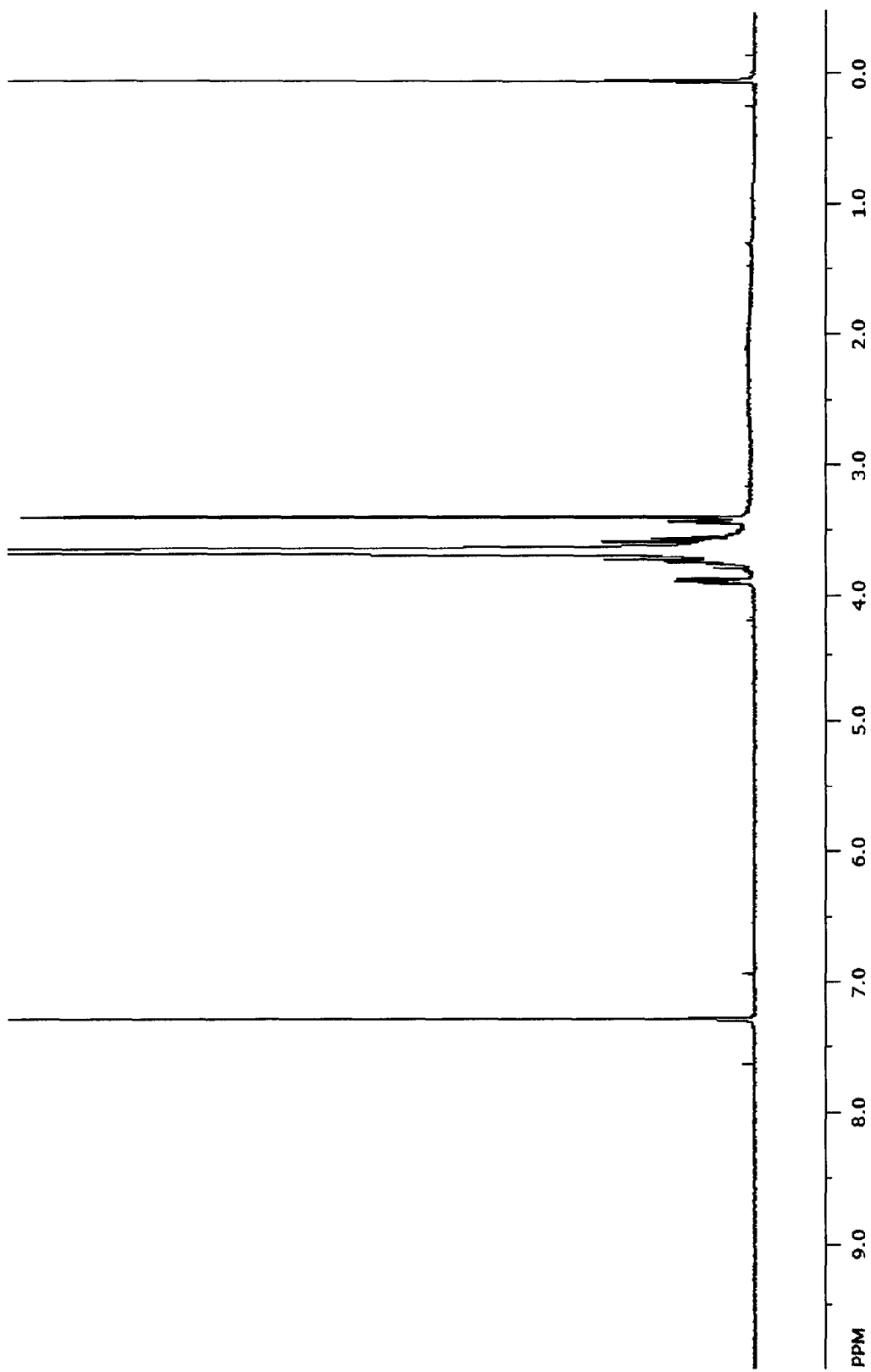
FIG. 5 illustrates analyzed results of $^1$H-NMR (in $CDCl_3$) of PEI-graft-(PEG;$PDOPA_{15}$) prepared in Example <1-6>.

After dissolving 0.5 g of the polyethyleneimine-graft-(polyethyleneglycol;polyDOPA) synthesized in Example <1-5> in DMF (30 ml), 8 ml of piperidine was added thereto. 15 minutes after reaction, the reaction product was precipitated in diethylether to obtain a polyethyleneimine-graft-(polyethyleneglycol;polyDOPA) in which a protective hydroxyl group of DOPA is de-protected. (Yield, molar ratio 1:5=80% [FIGS. 2 and 3], molar ratio 1:15=81% [FIGS. 4 and 5]).

The following Table 1 shows assayed results of a structure of the mussel adhesive protein-mimetic biocompatible dispersion stabilizer of the present invention and characteristics thereof, wherein the structure of a polymeric copolymer and characteristics thereof have been assayed through $^1$H-NMR and UV-Vis spectroscopy and using a fluorescent label.

TABLE 1

Analysis of structure and characteristics of mussel adhesive protein-mimetic biocompatible dispersion stabilizer

| Sample code | Copolymer | PEG $M_n$ | PEI $M_n$ | Molar ratio along with individual materials[a] | | | $M_n$[a] | CMC (g/L)[b] |
| --- | --- | --- | --- | --- | --- | --- | --- | --- |
| | | | | PEG | PEI | DOPA | | |
| MIL0 | PEI-graft-PEG | 5,000 | 1,800 | 8 | 1 | — | 41,800 | — |
| MIL1 | PEI-graft-(PEG; PDOPA) | 5,000 | 1,800 | 8 | 1 | 5 | 42,800 | 0.015 |
| MIL2 | PEI-graft-(PEG; PDOPA) | 5,000 | 1,800 | 8 | 1 | 15 | 44,800 | 0.005 |

[a]$M_n$: number average molecular weight, which is assayed using $^1$H-NMR and UV-Vis spectra
[b]CMC: Critical Micelle Concentration, which is assayed using a fluorescent label (Hoechst 33342)

Example 2

Synthesis of Iron Oxide Nanoparticles Stabilized by Mussel Adhesive Protein-Mimetic Biocompatible Dispersion Stabilizer 10 mg of magnetic nanoparticles ($Fe_3O_4$) which were synthesized in an organic solvent and stabilized with oleic acid, as well as 60 mg of mussel adhesive protein-mimetic biocompatible dispersion stabilizers (MIL1 and MIL2, respectively), were dispersed in 10 ml of chloroform ($CHCl_3$) and agitated at room temperature for 30 minutes. After evaporating chloroform ($CHCl_3$) and adding distilled water to the residue, the dispersed product was filtrated through a 200 nm syringe filter (MCE syringe filter, Fisher Scientific). After centrifuging to remove unreacted stabilizer, filtration was repeated 3 to 5 times using a spin filter (Millipore, 10K NMWL, 3000 rpm, 10 min). The resultant product was dispersed in an aqueous system having a pH 7.

Example 3

Synthesis of Manganese Oxide Nanoparticles Stabilized by Mussel Adhesive Protein-Mimetic Biocompatible Dispersion Stabilizer 10 mg of manganese oxide nanoparticles (MnO) which were synthesized in an organic solvent by the same procedure described in Example 2, were stabilized using the mussel adhesive protein-mimetic biocompatible dispersion stabilizers (MIL1 and MIL2, respectively) and then dispersed in water.

Example 4

Synthesis of Gold Nanoparticles Stabilized by Mussel Adhesive Protein-Mimetic Biocompatible Dispersion Stabilizer 10 mg of gold nanoparticles (Au) which were synthesized in an organic solvent by the same procedure described in Example 2, were stabilized using the mussel adhesive protein-mimetic biocompatible dispersion stabilizers (MIL1 and MIL2, respectively) and then dispersed in water.

Example 5

Synthesis of Quantum Dot Nanoparticles Stabilized by Mussel Adhesive Protein-Mimetic Biocompatible Dispersion Stabilizer 10 mg of quantum dot (CdSe/ZnS) nanoparticles which were synthesized in an organic solvent by the same procedure described in Example 2, were stabilized using the mussel adhesive protein-mimetic biocompatible dispersion stabilizers (MIL1 and MIL2, respectively) and then dispersed in water.

Example 6

Synthesis of Other Inorganic Nanoparticles Stabilized by Mussel Adhesive Protein-Mimetic Biocompatible Dispersion Stabilizer The following inorganic nanoparticles which were synthesized by the same procedure described in Example 2, were stabilized using the mussel adhesive protein-mimetic biocompatible dispersion stabilizers (MIL1 and MIL2, respectively) and then dispersed in water.

TABLE 2

|  | MIL1 | | MIL2 | |
|---|---|---|---|---|
| Inorganic nanoparticles | Size of nanoparticle (nm) | Hydro-dynamic diameter[a] (nm) | Size of nanoparticle (nm) | Hydro-dynamic diameter[a] (nm) |
| ZnO | 20 | 28 | 20 | 29 |
| CdS | 6 | 9 | 6 | 11 |
| CoFeO$_4$ | 12 | 15 | 12 | 18 |
| FePt | 10 | 14 | 10 | 18 |
| GdO | 25 | 34 | 25 | 36 |

Figure 6:
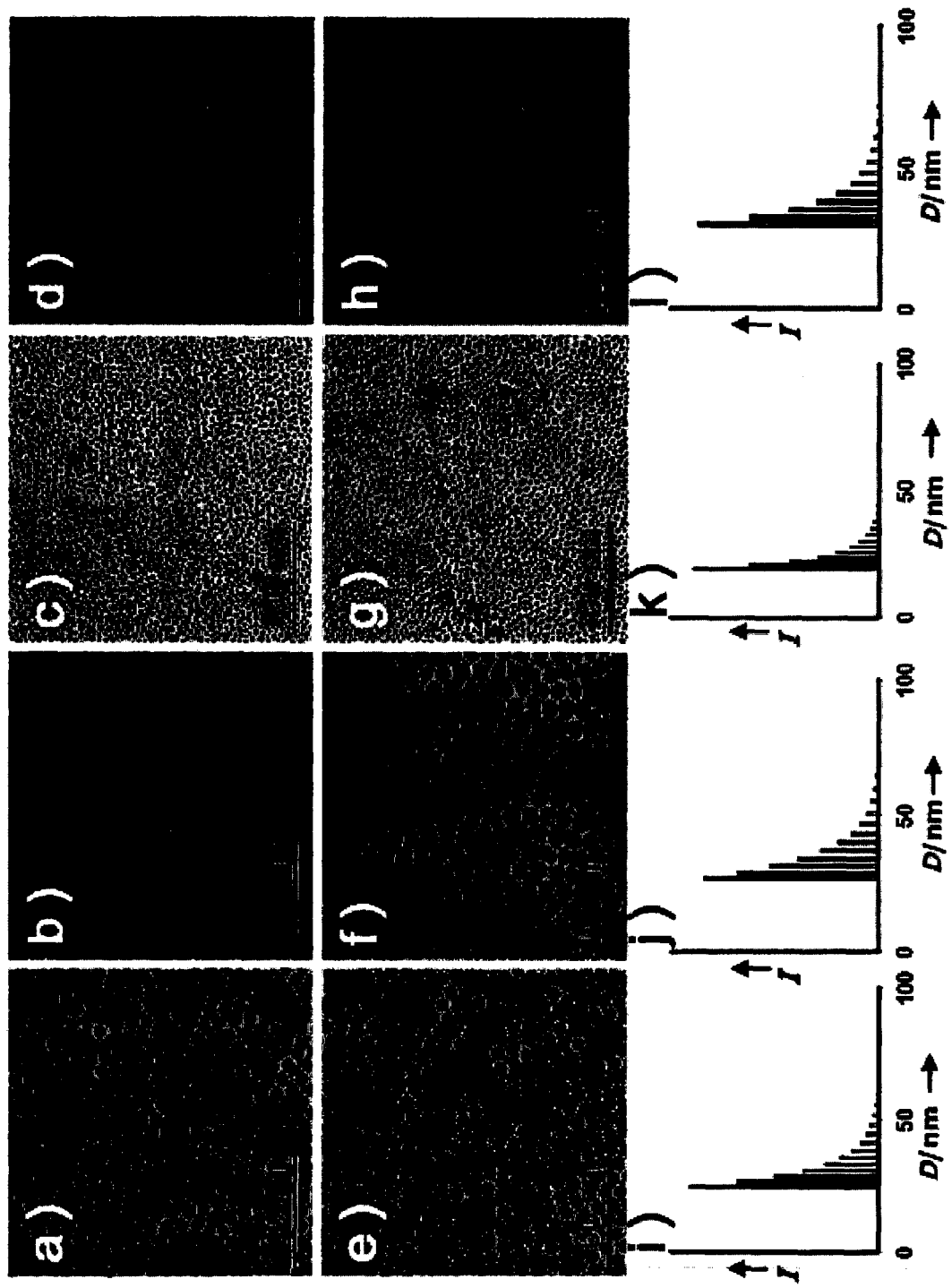
FIG. 6 illustrates transmission electron microscopy (TEM) images of nanoparticles (a: 11 nm $Fe_3O_4$, b: 13 nm MnO, c: 5 nm Au, d: 3 nm CdSe/ZnS) dispersed before stabilization, as well as nanoparticles (e: 11 nm $Fe_3O_4$, f: 13 nm MnO, g: 5 nm Au, h: 3 nm CdSe/ZnS), which are dispersed in water after stabilization thereof using a mussel adhesive protein-mimetic biocompatible dispersion stabilizer (MIL2); and particle sizes of various nanoparticles stably dispersed in water using a mussel adhesive protein-mimetic biocompatible dispersion stabilizer and by means of a dynamic light scattering (DLS) device (i:$Fe_3O_4$, j:MnO, k: Au, l:CdSe/ZnS)

[a]Hydro-dynamic diameter: a number average size measured by DLS in a dispersed condition in an aqueous system FIG. 6 illustrates transmission electron microscopy (TEM) images of various nanoparticles (a: 11 nm Fe$_3$O$_4$, b: 13 nm MnO, c: 5 nm Au, d: 3 nm CdSe/ZnS) dispersed before stabilization, as well as nanoparticles (e: 11 nm Fe$_3$O$_4$, f: 13 nm MnO, g: 5 nm Au, h: 3 nm CdSe/ZnS), which are dispersed in water after stabilization thereof using the mussel adhesive protein-mimetic biocompatible dispersion stabilizer (MIL2) prepared according to the inventive method.

According to the TEM images in FIG. 6, it can be understood that a variety of nanoparticles stably dispersed in water, using the mussel adhesive protein-mimetic bio-compatible dispersion stabilizer prepared by the inventive method, have substantially the same morphology and size as those of different kinds of nanoparticles dissolved in a hydrophobic solvent before adding the foregoing copolymer. Also, it was found that such results are not substantially changed even after addition of the dispersion stabilizer.

Meanwhile, i, j, k and l in FIG. 6 illustrate particle sizes of various nanoparticles (i:Fe$_3$O$_4$, j:MnO, k: Au, l:CdSe/ZnS) stably dispersed in water using a mussel adhesive protein-mimetic biocompatible dispersion stabilizer (MIL2) and by the DLS method. It was demonstrated that the foregoing nanoparticles have uniform and stable particle sizes of 11 nm, 13 nm, 5 nm and 3 nm, respectively.

Figure 7:
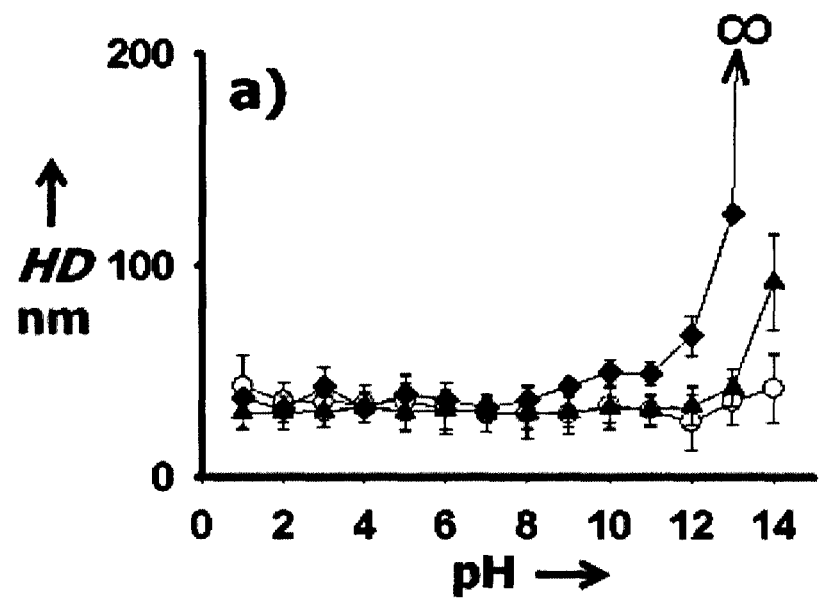
FIG. 7 illustrates experimental results of stabilities of nanoparticles before stabilization and iron oxide ($Fe_3O_4$) dispersed and stabilized in water using a mussel adhesive protein-mimetic dispersion stabilizer, along with various pH values and ionic concentrations, wherein the hydrodynamic diameter (HD) is measured using the DLS device, followed by comparison of measured results (MIL0 (♦), MIL1 (▲) and MIL2 (○))
Figure 7:
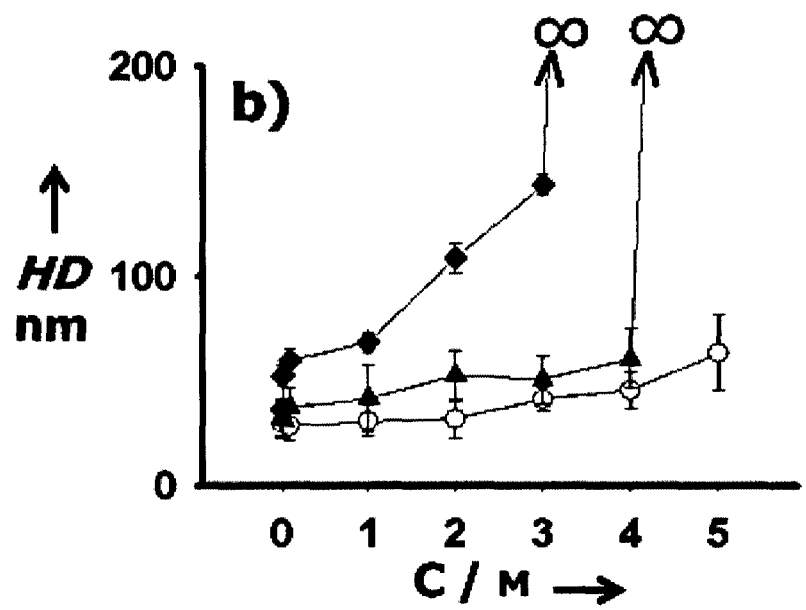

FIG. 7 demonstrates that nanoparticles (Fe$_3$O$_4$) were dispersed and stabilized in an aqueous system, using the mussel adhesive protein-mimetic dispersion stabilizer prepared according to the inventive method, along with various pH values and ionic concentrations. More particularly, it can be seen that, compared to the nanoparticles dispersed and stabilized by the dispersion stabilizer without DOPA (FIG. 7, MIL0 (♦)), the nanoparticles dispersed and stabilized using the biocompatible dispersion stabilizer prepared according to the present invention (FIG. 7, MIL1 (▲) and MIL2 (○)) are more stable at various pH values and concentrations.

Figure 8:
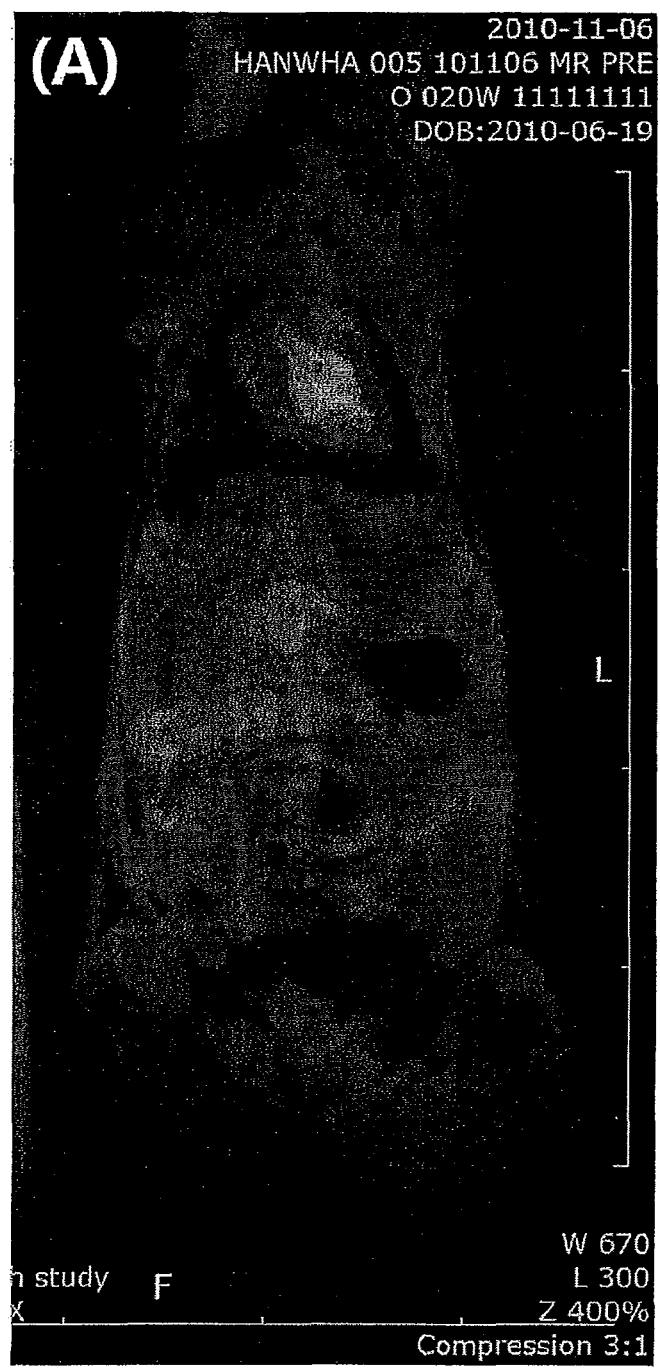
FIGS. 8-10 are in vivo magnetic resonance imaging (MRI) images of stabilized iron oxide by the mussel adhesive protein-mimetic biocompatible dispersion stabilizer (MIL2), including images of measured results before (FIG. 8), 24 hours after (FIG. 9), and 48 hours after (FIG. 10) administration of the stabilizer.
Figure 9:
Figure 10:

FIGS. 8-10 are in vivo magnetic resonance imaging (MRI) images obtained using nanoparticles (Fe$_3$O$_4$) dispersed and stabilized by the mussel adhesive protein-mimetic biocompatible dispersion stabilizer (MIL2) as a contrast agent through an MRI device. In this regard, from images obtained before (FIG. 8), 24 hours after (FIG. 9), and 48 hours after (FIG. 10) administration of the stabilizer, favorable stability in blood flow and prolonged half-life (that is, increased life span) in blood are demonstrated. Also, the Fe$_3$O$_4$ nanoparticles dispersed by the dispersion stabilizing agent showed good performance as an MRI contrast agent. With reference to the MRI images of FIGS. 8-10, it is confirmed that the organs of mouse darkened after the injection of Fe$_3$O$_4$ nano particles which were modified by MIL2. Consequently, it is confirmed that the foregoing nanoparticles may be utilized as a contrast agent for medical use according to the present invention.

INDUSTRIAL APPLICABILITY

According to the present invention, a mussel adhesive protein-mimetic biocompatible dispersion stabilizer capable of modifying the surface of nanoparticles and stably dispersing the same in an aqueous medium may be synthesized. The dispersion stabilizer prepared according to the present invention has polyDOPA formed through multi-initiative polymerization, in turn having at least one unit of DOPA per molecule, that is multiple interaction ligands (MIL) and exhibiting a high bonding strength to a hydrophilic surface. Since the prepared dispersion stabilizer according to the present invention has a positive charge, it may impart additional electrostatic bonding force to the surface of nanoparticles having a negative charge. Moreover, since numerous polyethyleneglycol molecules having hydrophilic property are bonded to branches of a branch type polyethyleneimine, high aqueous dispersion stabilization may be achieved through hydrophilic property and stereoscopic effects. Accordingly, the biocompatible dispersion stabilizer prepared as described above may enable stable dispersion of nanoparticles in an aqueous medium, thereby being applicable in various fields including, for example: nano-electronic convergence technologies such as Q-Dot light-emitting devices; bio-imaging applications such as a magnetic resonance imaging (MRI) contrast agent; tissue engineering applications such as cell treatment; biomedical applications such as hyperthermia, drug delivery, etc. Further, compared to nanoparticles dispersed by a dispersion stabilizers produced according to conventional techniques, superior dispersion stability may be achieved.

The invention claimed is:

1. A polyethyleneimine-graft-(polyethyleneglycol;poly(3, 4-dihydroxyphenylalanine)) copolymer (PEI-graft-(PEG; PDOPA)), consisting of polyethyleneglycol, polyethyleneimine and poly(3,4-dihydroxyphenylalanine), wherein the PDOPA is selected from L-PDOPA synthesized from N-carboxyl anhydride of L-DOPA (L-3,4-dihydroxy phenylalanine), D-PDOPA synthesized from N-carboxyl anhydride of D-DOPA(D-3,4-dihydroxy phenylalanine), and L,D-PDOPA synthesized from N-carboxyl anhydride of L,D-DOPA (L,D-3,4-dihydroxy phenylalanine), wherein PDOPA is represented by Structure [C]:

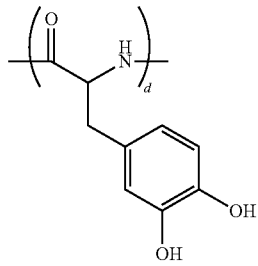

and wherein d ranges from 2 to 100.

2. The PEI-graft-(PEG;PDOPA) of claim 1, wherein the polyethyleneglycol has an average molecular weight of 300 to 50,000 and at least one terminal end group selected from a hydroxyl group and a carboxyl group.

3. The PEI-graft-(PEG;PDOPA) of claim 1, wherein the polyethyleneimine is a branch type polyethyleneimine having a number average molecular weight of 100 to 10,100.

4. The PEI-graft-(PEG;PDOPA) of claim 1, wherein the polyethyleneglycol is represented by Structure A:

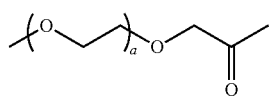

[A]

wherein a ranges from 2 to 1200, wherein the polyethyleneimine is represented by Structure [B]:

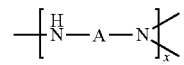

wherein A is a branch type polyethyleneimine and x ranges from 1 to 100.

5. The PEI-graft-(PEG;PDOPA) of claim 4, wherein the polyethyleneimine unit is represented by the following structure:

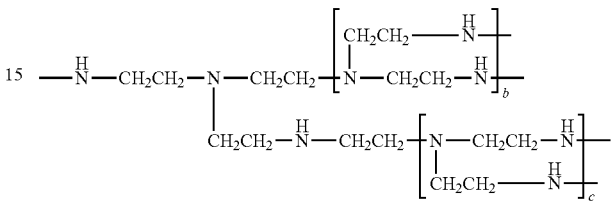

wherein each of b and c ranges from 1 to 100.

6. The PEI-graft-(PEG;PDOPA) of claim 1, wherein the molar ratio of polyethyleneimine-graft-polyethyleneglycol and the N-carboxyl anhydride of DOPA ranges from 1:1 to 1:50.

7. A method for preparing the polyethyleneimine-graft-(polyethyleneglycol; poly(3,4-dihydroxyphenylalanine)) copolymer (PEI-graft-(PEG;PDOPA)) of claim 1, comprising:
(a) grafting polyethyleneglycol with polyethyleneimine through covalent bonding, to form polyethyleneimine-graft-polyethyleneglycol;
(b) after protecting the hydroxyl groups of 3,4-dihydroxyphenylalanine (DOPA), synthesizing the N-carboxyl anhydride of DOPA in the presence of a triphosgene catalyst; and
(c) reacting polyethyleneimine-graft-polyethyleneglycol prepared in operation (a) and the N-carboxyl anhydride of DOPA synthesized in operation (b) in an organic solvent, to prepare the PEI-graft-(PEG;PDOPA).

8. The method of claim 7, wherein the organic solvent in operation (c) is at least one selected from dimethyl sulfoxide, tetrahydrofuran and chloroform.

9. The method of claim 7, wherein the molar ratio of polyethyleneimine-graft-polyethyleneglycol and the N-carboxyl anhydride of DOPA in operation (c) ranges from 1:1 to 1:50.

10. The method of claim 7, further comprising:
(d) de-protecting the protected hydroxyl groups.

11. Nanoparticles dispersed in an aqueous medium, using the PEI-graft-(PEG;PDOPA) of claim 1, as a dispersion stabilizer.

12. The nanoparticles of claim 11, wherein the nanoparticles are one or more selected from the group consisting of a metal, a metal chalcogenide, a metal oxide, a magnetic substance, a magnetic alloy, a semiconductor material and a heterojunctioned material.

13. The nanoparticles of claim 12, wherein the metal is one or more selected from the group consisting of Pd, Pt, Au, Cu and Ag;
wherein the metal calcogenide is $M_xE_y$, wherein M=Ti, V, Cr, Mn, Fe, Co, Ni, Cu, Zr, Mo, Ru, Rh, Ag, W, Re, Ta, Hf, Zn or Cd; E=O, S or Se; $0<x\leq3$; $0<y\leq5$;
wherein the metal oxide is one or more selected from the group consisting of titanium oxide, vanadium oxide, chromium oxide, manganese oxide, iron oxide, cobalt oxide, nickel oxide, copper oxide, zirconium oxide, molybdenum oxide, ruthenium oxide, rhodium oxide, silver oxide, tungsten oxide, rhenium oxide, tantalum oxide, hafnium oxide and zinc oxide;

wherein the magnetic substance is one or more selected from the group consisting of Co, Mn, Fe, Ni, Gd, $MM'_2O_4$ and $M_xO_y$, wherein M or M'=Co, Fe, Ni, Mn, Zn, Gd, Cr; x ranges from 1 to 3; and y ranges from 1 to 5, respectively;

wherein the magnetic alloy is one or more selected from the group consisting of CoCu, CoPt, FePt, CoSm, NiFe and NiFeCo;

wherein the semiconductor material is one or more selected from the group consisting of elements selected from Group 2, Group 3, Group 4, Group 5, and Group 6 respectively.

14. The nanoparticles of claim 12, wherein the heterojunctioned material is a core-shell material.

15. The nanoparticles of claim 13, wherein the metal oxide is iron oxide.

16. The nanoparticles of claim 15, wherein the metal oxide is one or more selected from the group consisting of FeO, $Fe_3O_4$(magnetite), $\alpha$-$Fe_2O_3$, $\beta$-$Fe_2O_3$, $\gamma$-$Fe_2O_3$(maghemite), $\epsilon$-$Fe_2O_3$, $Fe(OH)_2$, $Fe(OH)_3$, $\alpha$-FeOOH, $\beta$-FeOOH, $\gamma$-FeOOH, $\delta$-FeOOH, $Fe_5HO_8 \cdot 4H_2O$, $5Fe_2O_3 \cdot 9H_2O$, $FeOOH \cdot 4H_2O$, $Fe_8O_8(OH)_6(SO) \cdot nH_2O$, $Fe_{16}O_{16}(OH.SO_4)_{12-13} \cdot 10\text{-}12H_2O$, and a mixture of $Fe_3O_4$(magnetite) and $\gamma$-$Fe_2O_3$(maghemite).

17. The nanoparticles of claim 16, wherein the iron oxide is one or more selected from $Fe_3O_4$(magnetite), $\gamma$-$Fe_2O_3$ (maghemite), and a mixture thereof.

18. A colloidal solution containing the nanoparticles of claim 11 dispersed in an aqueous medium.

19. The colloidal solution of claim 18, further comprising an MRI contrast agent.

* * * * *